United States Patent
Lowy

(10) Patent No.: US 9,733,226 B1
(45) Date of Patent: Aug. 15, 2017

(54) APPARATUS AND METHOD FOR MEASURING A GAS

(71) Applicant: Jonathan David Lowy, Auckland (NZ)

(72) Inventor: Jonathan David Lowy, Auckland (NZ)

(73) Assignee: RIPETIME LIMITED, Auckland (NZ)

( * ) Notice: Subject to any disclaimer, the term of this patent is extended or adjusted under 35 U.S.C. 154(b) by 0 days.

(21) Appl. No.: 15/013,109

(22) Filed: Feb. 2, 2016

(51) Int. Cl.
 *G01N 1/22* (2006.01)
 *G01N 33/00* (2006.01)
 *G01N 1/40* (2006.01)

(52) U.S. Cl.
 CPC ....... *G01N 33/0047* (2013.01); *G01N 1/2214* (2013.01); *G01N 1/2226* (2013.01); *G01N 1/2273* (2013.01); *G01N 1/405* (2013.01); *Y10T 436/216* (2015.01); *Y10T 436/25875* (2015.01)

(58) Field of Classification Search
 CPC ...... G01N 1/22; G01N 1/2214; G01N 1/2226; G01N 1/2273; G01N 1/40; G01N 1/405; G01N 33/0047; Y10T 436/216; Y10T 436/25; Y10T 436/25875
 USPC ..... 436/139, 142, 147, 174, 181; 422/83, 88
 See application file for complete search history.

(56) References Cited

U.S. PATENT DOCUMENTS

| | | | | |
|---|---|---|---|---|
| 5,142,143 A * | 8/1992 | Fite | ........................ | G01M 3/202 |
| | | | | 250/281 |
| 6,244,096 B1 * | 6/2001 | Lewis | ........................ | A61B 5/00 |
| | | | | 422/78 |
| 8,158,933 B2 * | 4/2012 | Taylor | ..................... | G01N 1/405 |
| | | | | 250/281 |
| 8,668,873 B2 * | 3/2014 | Almirall | ................ | G01N 1/405 |
| | | | | 422/527 |
| 2004/0210099 A1 * | 10/2004 | Shiratori | ................ | A23B 7/152 |
| | | | | 585/821 |
| 2005/0007119 A1 * | 1/2005 | Belyakov | ................. | G01N 1/22 |
| | | | | 324/464 |

OTHER PUBLICATIONS

Sklorz et al. Sensors and Actuators B, vol. 170, Dec. 1, 2010, pp. 21-27.*
Dow et al. IEEE Sensors Journal, vol. 12, No. 7, Jul. 2012, pp. 2528-2534.*

* cited by examiner

*Primary Examiner* — Maureen Wallenhorst
(74) *Attorney, Agent, or Firm* — Bacon & Thomas, PLLC

(57) ABSTRACT

In a measuring method for measuring an atmospheric concentration of a compound, such as a volatile organic compound (VOC), an adsorptive element is provided within a target atmosphere for a period of time to allow adsorption of a compound of interest for measurement, and then removed from the target atmosphere, and placed within a closed measuring space. The adsorptive element is heated within the measuring space to cause de-adsorption of the compound into the closed measuring space, and a concentration of the de-adsorbed compound is measured. A concentration of the compound in the target atmosphere is determined based on the concentration of the compound within the closed measuring space. The adsorptive element may be formed of an adsorptive material such as carbon fibers, cellulose or other adsorptive materials, and a binder. The adsorptive element may be optimized for adsorption of a specific compound.

20 Claims, 6 Drawing Sheets

APPARATUS AND METHOD FOR MEASURING A GAS

FIELD OF THE INVENTION

The present invention relates to an apparatus and method for measuring a concentration of an aerosolized or gaseous compound, such as a volatile organic compound (VOC), in an atmosphere, and more particularly an apparatus and method using an adsorptive collecting element for collection and measurement of the VOC.

BACKGROUND

The ability to measure an atmospheric concentration of an aerosolized or gaseous compound, such as a volatile organic compound, at relatively low levels, has practical and useful applications, but presents technological challenges.

For example, ethylene is a ubiquitous problem in the fresh produce supply chain. However, measurements of the gas are rarely taken and even more rarely relied upon. Even when used, such measurements often yield highly unreliable results.

While ethylene emitted from produce can be correlated to a degree of ripeness of the produce, almost all ripeness testing is performed using either manual examination by skilled hands, or by destructive cell collapse compression tests wherein cell load capacity is directly proportional to and calibrated to ripeness. Both entail high labour cost, high fruit loss and relatively low accuracy. And, neither test method is informative about the early stages of ripeness, so these methods simply don't work as predictors.

Ethylene control is commonly used across many sectors, but is not typically used for ripeness analysis. And, it is believed that analysis of any VOCs other than ethylene, such as heavier compounds relating to flavor and scent that appear to be present in trace quantities at early phases in the development post-harvest, is unknown, although such other VOCs are believed to provide rich data about fruit condition. Improved measurement capability and sensitivity, such as in a range of 10-30 parts per billion atmospheric, can provide useful tools for early and mid stage fruit analysis.

PPM sensors for, for example, ethylene and a range of other VOCs, are cheap, reliable and simple to use, whereas known sensors suitable in a parts per billion (PPB) range are both expensive and unreliable.

Precision sensors that can test PPB atmospheres cost $10k and upwards to $1M and take minutes to hours to take single readings, usually by means of long slow flow or super precise measurement tools such as gas chromatography-mass spectrometry (GCMS) and photo acoustic spectrometry. These methods are only suited to very low volume testing.

Hence, a low cost and accurate method and apparatus for measuring low PPB atmospheric concentrations of a substance such as a volatile organic compound is desired.

It is therefore an object of the present invention to provide an apparatus and method for measuring a concentration of a volatile organic compound (VOC) in an atmosphere, and in particular for performing such measurements at low concentration levels.

SUMMARY

The present invention exploits an adsorptive tendency of certain materials, such as carbon, to capture an aerosolized or gaseous substance within an atmosphere, for providing the adsorbed sample to a test device. For example, an adsorptive element may be provided in a fruit box or storage environment to collect a sample of a volatile organic compound or a gas related to a ripeness, or other developmental aspect, of fruit, wherein the adsorptive element may be subsequently removed to a test device.

The apparent surface area of an adsorber of the invention is significantly larger than the physical exterior of the adsorber patch, so that a capacity for adsorption of a substance is greatly increased. For example, a carbon adsorber in one embodiment of the invention has an effective surface area significantly greater than a typical fruit box (including fruit surfaces), providing a substantially greater surface area for adsorption than the physical external dimensions of the adsorber itself.

When desorbed by heating in a small, closed volume, the adsorbed gasses are released suddenly and raise the concentration in the small test volume to levels that are much higher than the original atmosphere. This presents as the adsorber as acting as an intermediary concentrator or amplifier. It has been found that concentration levels in the test chamber are 300 to 1000 or more times the original atmospheric concentration. It is believed that concentration levels in the test chamber as high as 10,000 times the original atmospheric concentration may be achieved.

This enables readings in parts per million (PPM) that represent atmospheres whose VOC levels are in parts per billion.

Thus a low cost PPM sensor can be used for measurement of the collected sample, providing a baseline for interpolation back to a measurement of an atmosphere whose concentration levels are significantly less concentrated.

According to one embodiment of the present invention, use of sensitized adsorber as a collector provides an amplification/sensitivity increase in collection of a VOC to be measured within an atmosphere of interest for measurement, such that using open atmosphere adsorption followed by limited volume closed atmosphere de-adsorption allows for measurements of the VOC in the atmosphere of interest at significantly lower levels than possible by conventional direct measurement of the atmosphere of interest. These and other features, aspects, and advantages of the present invention will become better understood with regard to the following description, appended claims, and accompanying drawings.

DETAILED DESCRIPTION OF VARIOUS EMBODIMENTS

Figure 1:
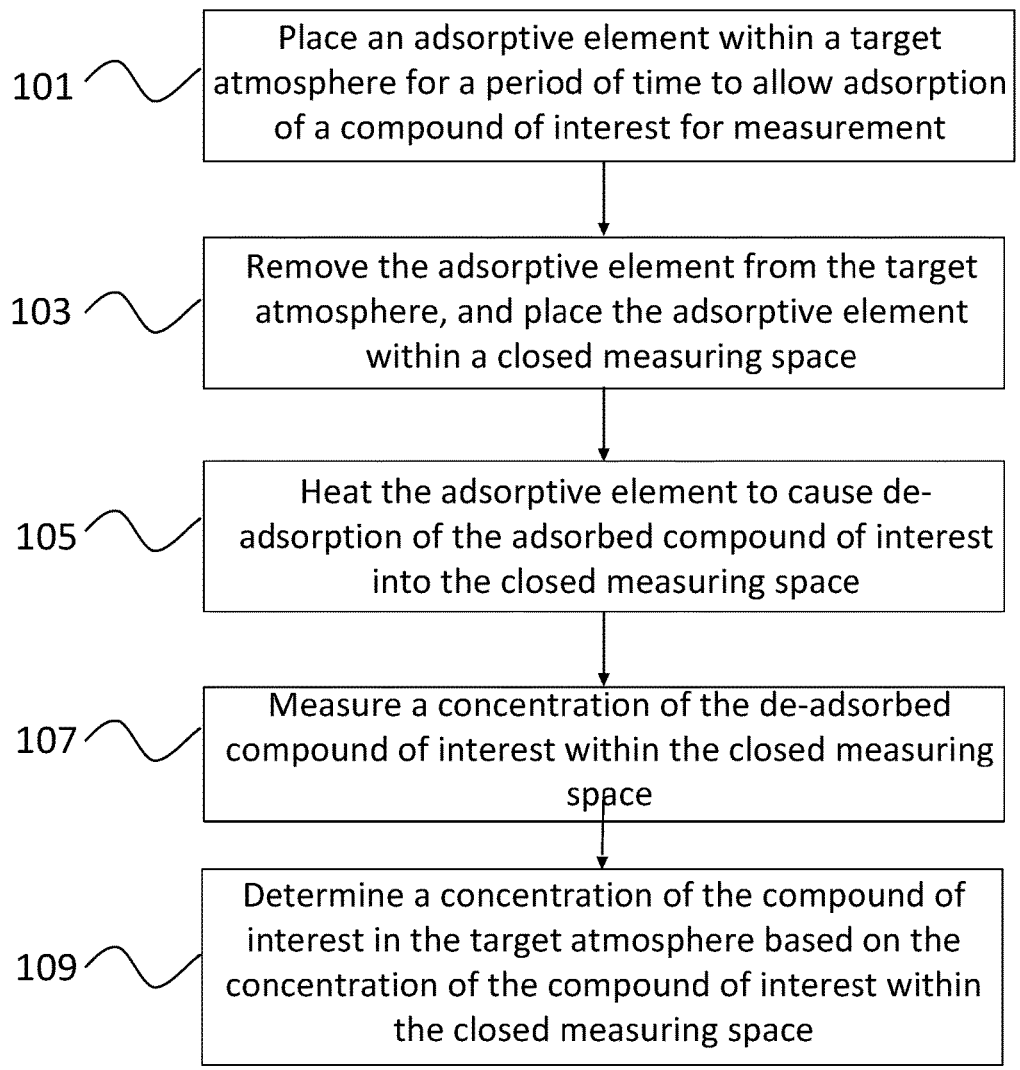
FIG. 1 is a flowchart showing a method for measuring an atmospheric concentration of a volatile organic compound using an adsorptive element.
Figure 2:
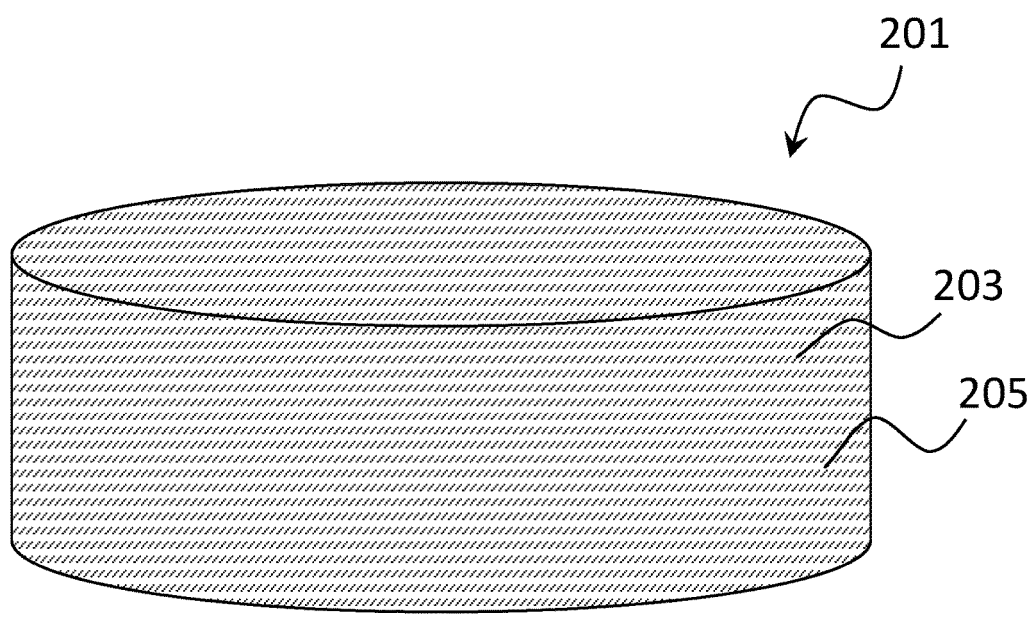
FIG. 2 illustrates an embodiment of an adsorptive element of the present invention.

Referring to FIG. 1, a measuring method for measuring an atmospheric concentration of a compound, such as a volatile organic compound (VOC), can be broadly described as comprising steps of: providing an adsorptive element within a target atmosphere for a period of time to allow adsorption of a compound of interest for measurement; removing the adsorptive element from the target atmosphere, and placing the adsorptive element within a closed measuring space; heating the adsorptive element to cause de-adsorption of the compound of interest into the closed measuring space; measuring a concentration of the de-adsorbed compound of interest within the within the closed measuring space; and determining a concentration of the compound of interest in the target atmosphere based on the concentration of the compound of interest within the closed measuring space.

An adsorptive element 201 of the invention is, in one embodiment, a carbon mass, which may be formed of carbon particles 203 such as carbon fibers, carbon nanofibers, carbon nanotubes and the like. The carbon particles 203 may be formed into a disk or "pill" in certain embodiments. The disk or pill may be cast from a wet slurry comprising the carbon particles 203 and a binder 205. Suitable binders 205 include, but are not limited to, water soluble phase change polymers, such as poly vinyl acetate, or wood glue. In certain embodiments, a wet slurry includes carbon particles with poly vinyl acetate at about 2-8% of the weight of the particles.

Polysiloxanes as well as polyvinylalcohol are also suitable binders. Copper oxide (CuO) may be included, such as for example a mixture of carbon nanofibers, CuO and polyvinylalcohol. In a mixture of carbon nanofibers, together with CuO (at about 6-18% of the weight of the nanofibers) and polyvinylalcohol (at about 15% of the weight of the nanofibers), a resulting adsorber has been found effective to detect ethylene in less-than 100 ppb concentrations.

It is advantageous that a ratio of the carbon particles 203 to the binder 205 is such as to maximize porosity of the disk (hence maximizing an exposed surface area of the carbon particles 203), while at the same time minimizing shedding of the carbon particles 203. It can be recognized that if too much of the binder is used, the disk becomes insufficiently porous for good adsorption, while if too little of the binder is used, the disk may be prone to spalling, releasing loose carbon particles into the environment. Prevention of spalling becomes especially desirable if the adsorptive element is used in proximity to food items.

In addition to a carbon based adsorber, other adsorbing materials may be used. For example, in certain embodiments an adsorber may be formed of cellulose, cellulose coated with silver particles, silver nitrate, a mixture of polypyrrole and silver nitrate, silver nanoparticles or the like. For example, cellulose may be coated with mixture of polypyrrole and silver nitrate at about 0.1M concentration. Cellulose based adsorbers have been found effective to detect ethylene at as low as 10 ppb concentrations, when the sample is heated at 100-125° C.

Similarly, an adsorber may be formed of alumide, alumide coated with silver particles, silver nitrate, a mixture of polypyrrole and silver nitrate, silver nanoparticles or the like. Further, mesoporous silica is another suitable adsorbant.

An ionic liquid may be incorporated to further enhance adsorption. For example, in the case of ethylene, an ionic liquid used as an ethylene trapping agent aides in ionization of silver nanoparticles (to Ag+), which binds to electron donor groups in ethylene, helping to remove ethylene from the surrounding atmosphere.

As described above and with reference to FIG. 1, the adsorptive element 201 in use is placed in a target atmosphere for a time period during which the VOC will be adsorbed. Subsequently, the adsorptive element 201 is removed from the target atmosphere, placed within an enclosed, sealed measuring space, and heated to cause de-adsorption of the collected VOC. In certain embodiments, a heater may be incorporated within a sealed measuring space of a measuring device, while in other embodiments a heater may be formed together with the adsorptive element 201 such as in an adsorptive tag 300.

Figure 3:
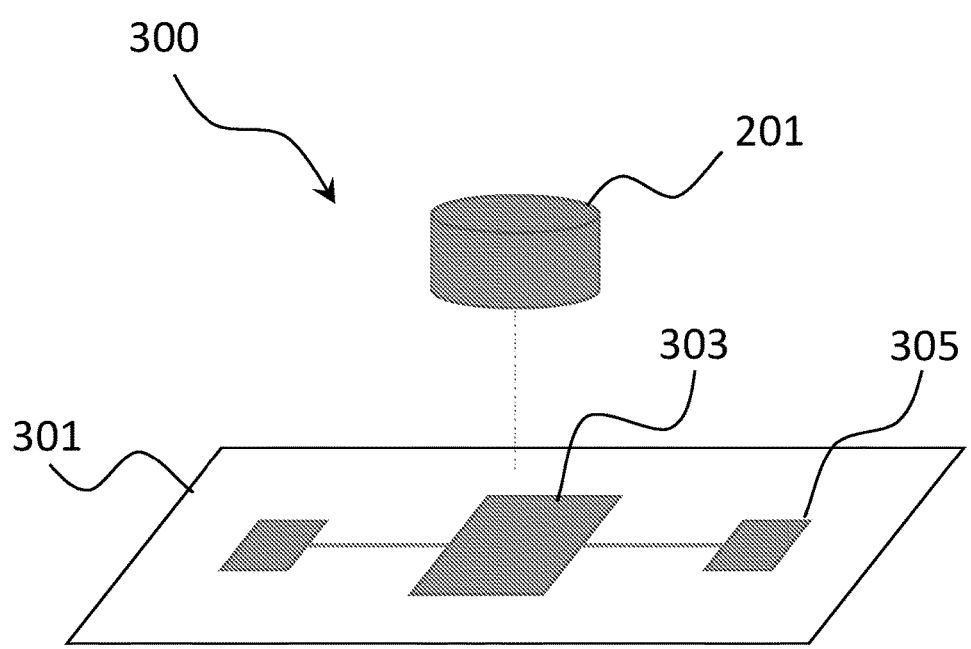
FIG. 3 is a diagrammatic depiction of an adsorptive tag including a substrate, heating element and adsorptive element.

A general arrangement for an adsorptive tag 300 is shown in FIG. 3, wherein a substrate 301 is provided with an electrical heating element 303 formed on or embedded in the substrate 301, electrical contact elements 305 are disposed on the substrate 301 and in electrical connection to the heating element such that an electrical current may be supplied to the electrical heating element 303 from a sampling or measurement device, and an adsorptive element 201 is disposed on the substrate 301 over the heating element 303.

Figure 4A:
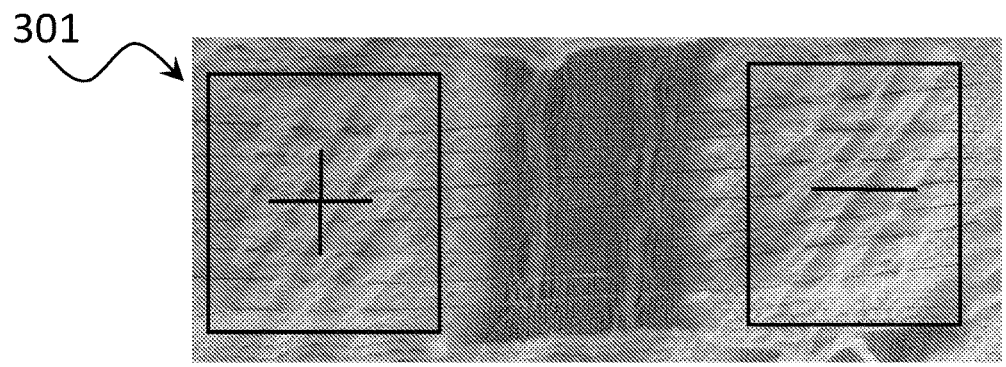
FIGS. 4a-4d illustrate certain possible configurations of an adsorptive tag.
Figure 4B:
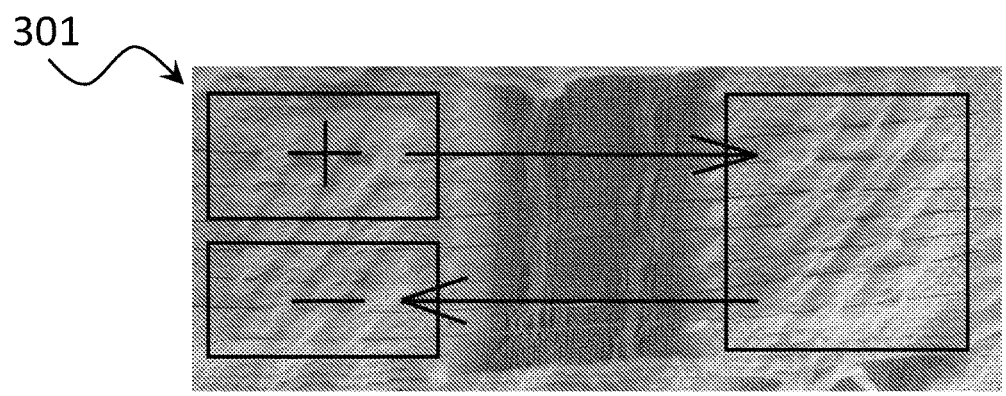
Figure 4C:
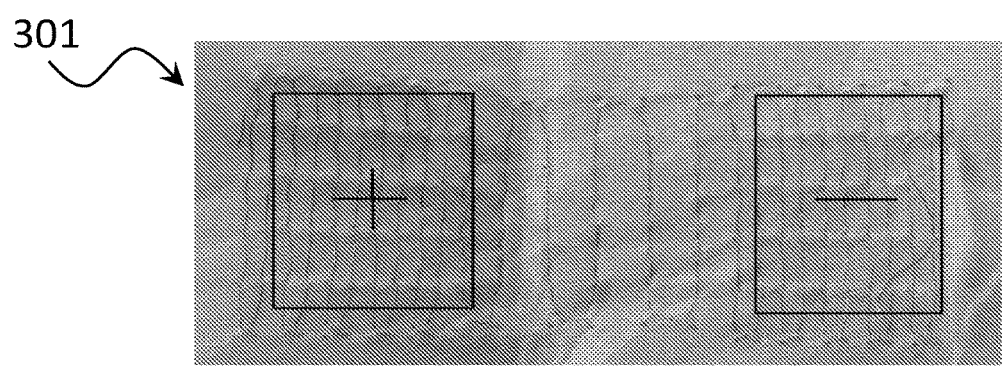

Referring to FIGS. 4a-4d, embodiments of a substrate 301 having an integral heating element are shown. Broadly speaking, the heating element 303 comprises one or more heating wires formed on, or embedded in, a substrate 301, and arranged such that an adsorptive element 201 may be disposed on the substrate 301, over the heating wires. In FIGS. 4a and 4b, a plurality of parallel heating wires of the heating element 303 are provided and arrayed such that positive and negative electrical contacts 305 may be provided at opposite ends of the wire array of the heating element, to provide an electric current for heating the heating wires of the heating element 303. In FIG. 4c, the heating element 303 comprises a single heating wire, arranged in a meander pattern.

In certain embodiments, the substrate 303 may be a woven or embroidered fabric, with the heating wires woven into the fabric such that at least end portions of the heating wires are exposed for electrical contact, defining electrical contact regions 305. The electrical contact regions 305 are arranged to make electrical contact with electrical terminals provided in a measuring device.

Figure 4D:
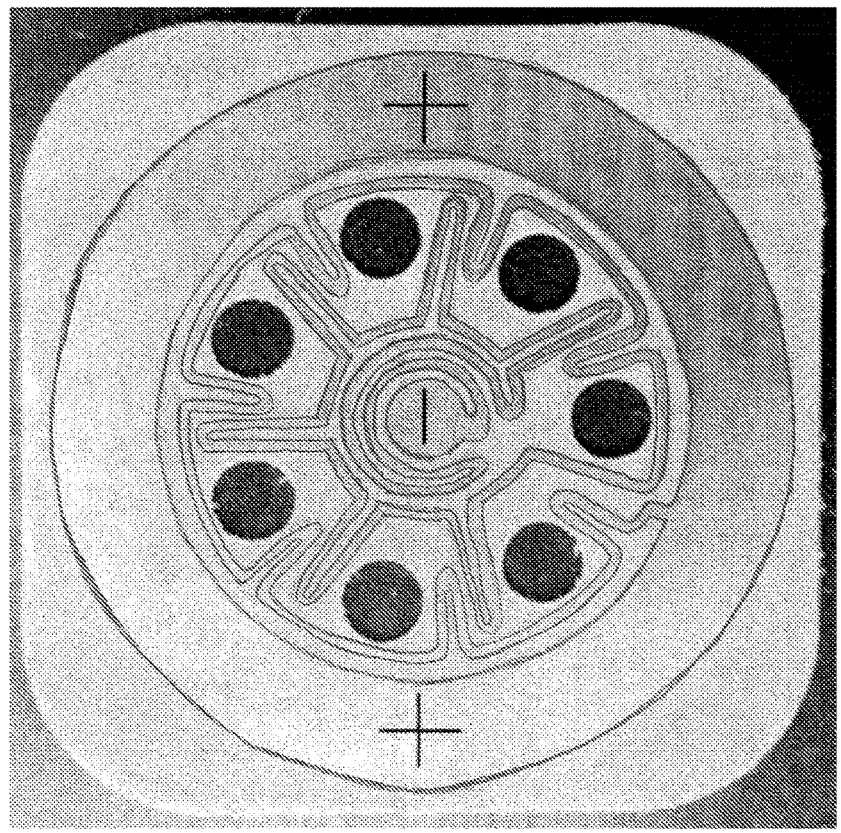

Alternatively, shown in FIG. 4d, a substrate 301 may be provided in the form of a circuit board substrate 401 with an etched foil heating element matrix 403. It can be recognized that porosity of the substrate, inherent to a fabric substrate, may facilitate dispersion of the de-adsorbed compound from the adsorbing element into the measuring space. Accordingly, apertures 405 may be formed through the circuit board substrate 401 to similarly facilitate dispersion such dispersion.

In certain embodiments, the adsorptive element may be optimized for adsorption of a particular compound, such as by addition of electroactive dopants.

Figure 5:
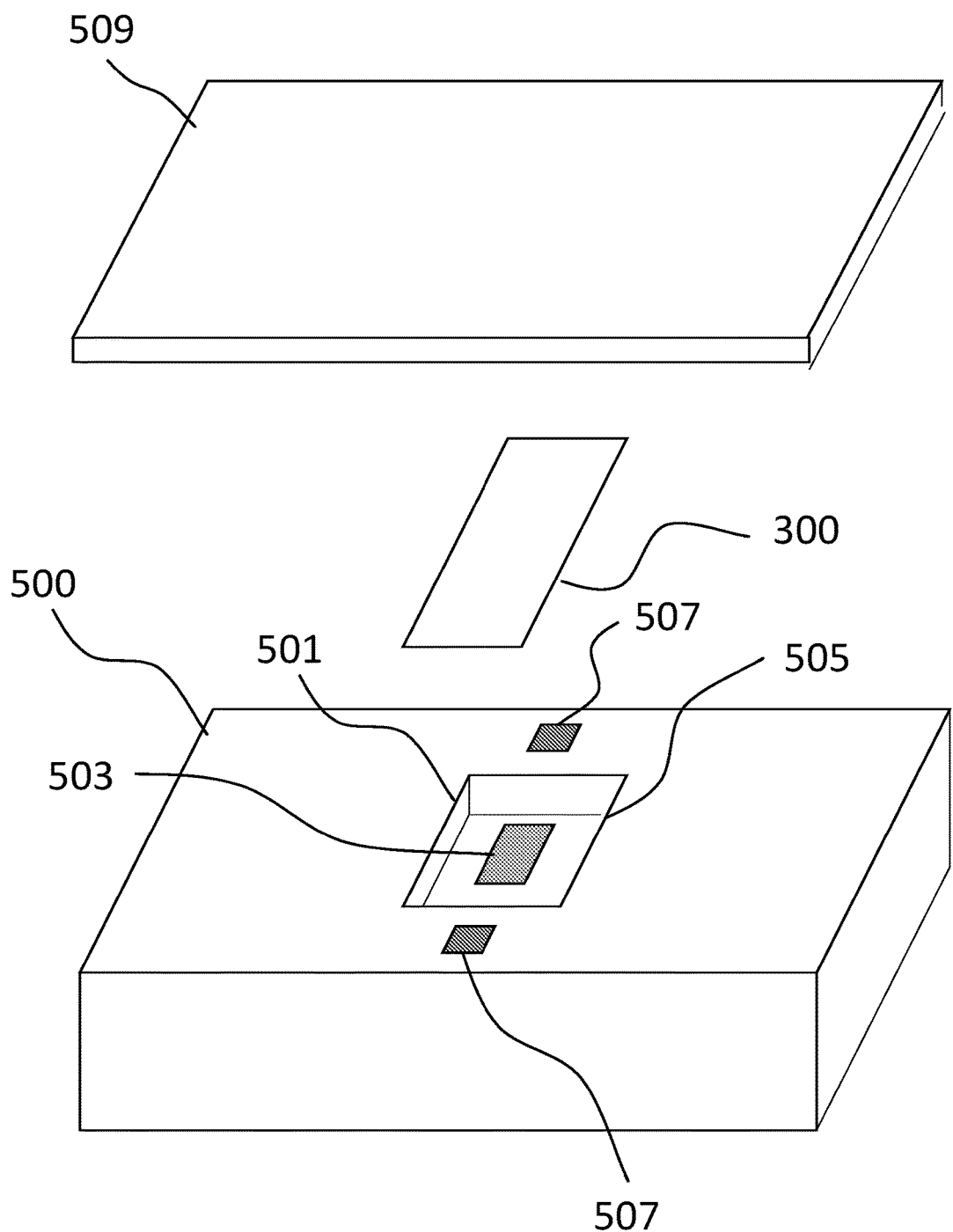
FIG. 5 is a diagrammatic view of a measuring device adapted to receive an adsorptive tag in a closed measuring space.

Referring to FIG. 5, a measuring device 500 is adapted to receive an adsorptive tag 300 in a closed measuring space 505. Within a body of the measuring device 500, a receiving space, or measuring space 505 is defined, where in the measuring space 505 is closed or closable such as by a cover 509. Within the measuring space 505 is disposed a sensor 503 which is adapted for measurement of a substance of interest, such as a volatile organic compound (VOC). In an illustrated embodiment, proximate to or within the measuring space 505, electrical terminals 507 are arranged to correspond with electrical contact elements 305 of the adsorptive tag 300 for supplying an electrical current to the heating element of the adsorptive tag 300. In alternative embodiments, a heating element may be disposed within the body of the measuring device such that the measuring device may be used with an adsorptive element or adsorptive tag lacking an integrated heating element.

A control circuit is provided to activate the heating element and the sensor 503, to obtain and display or report a measurement of the substance of interest within the measuring space 505. Referring again to FIG. 1, an adsorptive element such as the adsorptive tag 300 is placed within the measuring space 505, and the measuring space 505 is then closed. Following closure of the measuring space 505, the adsorptive element is heated, such as by applying an electrical current to the heating element, to cause de-adsorption of the compound of interest into the closed measuring space. A measurement of a concentration of the de-adsorbed compound of interest within the within the measuring space is taken by the sensor 503, from which can be determined a concentration of the compound of interest in the target atmosphere.

In view of the concentration, or amplification, of the compound of interest in the target atmosphere achieved by the adsorber, the concentration in the target atmosphere is determined as a function of the measured concentration, and the expected amplification. For example, considering an adsorber that achieves a 1000 times amplification, a measured value of 50 ppm would correspond to a 50 ppm concentration in the target atmosphere. Approximate amplifications resulting from this process are of the order of 300 to over 1000 times, and may be as high as 10,000 times.

It will be understood that the above-described embodiments of the invention are illustrative in nature, and that modifications thereof may occur to those skilled in the art. Accordingly, this invention is not to be regarded as limited to the embodiments disclosed herein, but is to be limited only as defined in the appended claims.

I claim:

1. A method for measuring an atmospheric concentration of a compound, comprising steps of:
   providing an adsorptive tag within a target atmosphere for a period of time to allow adsorption of a compound of interest for measurement, wherein the adsorptive tag comprises a substrate, a heating element disposed on or within the substrate and an adsorptive element disposed on the substrate over the heating element;
   removing the adsorptive tag from the target atmosphere after said period of time, and placing the adsorptive tag within a closed measuring space with electrical contacts of said heating element brought into connection with an electrical power source;
   heating the adsorptive element to cause de-adsorption of the compound of interest into the closed measuring space;
   measuring a concentration of the de-adsorbed compound of interest within the closed measuring space; and
   determining a concentration of the compound of interest in the target atmosphere based on the concentration of the compound of interest within the closed measuring space.

2. The method of claim 1, wherein said adsorptive element is a carbon based adsorptive element.

3. The method of claim 1, wherein said adsorptive element comprises a plurality of carbon particles.

4. The method of claim 3, wherein said plurality of carbon particles comprises carbon nano particles.

5. The method of claim 4, wherein said carbon nano particles are carbon nano tubes.

6. The method of claim 1, wherein said adsorptive element is a cellulose based adsorptive element.

7. The method of claim 6, wherein said cellulose based adsorptive element is coated with a polypyrrole/silver nitrate preparation.

8. The method of claim 1, wherein said adsorptive element is an alumide based adsorptive element.

9. The method of claim 1, wherein said adsorptive element comprises a plurality of silver nanoparticles.

10. An adsorptive tag for collecting and releasing a measurement sample, comprising:
    a substrate;
    a heating element disposed on or within said substrate;
    positive and negative electrical contacts disposed on said substrate and electrically connected with said heating element; and
    an adsorptive element disposed on said substrate over said heating element;
    wherein said substrate is configured for placement within a closed measuring device with said electrical contacts in contact with electrical terminals provided in the closed measuring device.

11. The adsorptive tag of claim 10, wherein said adsorptive element is a carbon based adsorptive element.

12. The adsorptive tag of claim 10, wherein said adsorptive element comprises a plurality of carbon particles.

13. The adsorptive tag of claim 12, wherein said plurality of carbon particles comprises carbon nano particles.

14. The adsorptive tag of claim 13, wherein said carbon nano particles are carbon nano tubes.

15. The adsorptive tag of claim 10, wherein said substrate is a fabric substrate.

16. The adsorptive tag of claim 15 wherein said heating element is a wire heating element woven into said fabric substrate.

17. The adsorptive tag of claim 10, wherein said adsorptive element is configured for adsorption of a volatile organic compound (VOC).

18. The adsorptive tag of claim 17, wherein said VOC is ethylene.

19. The adsorptive tag of claim 10, wherein said adsorptive element is a cellulose based adsorptive element.

20. The adsorptive tag of claim 19, wherein said cellulose based adsorptive element is coated with a polypyrrole/silver nitrate preparation.

* * * * *